United States Patent [19]
Kammerer et al.

[11] Patent Number: 5,941,439
[45] Date of Patent: Aug. 24, 1999

[54] APPLICATOR AND METHOD FOR DEPLOYING A SURGICAL FASTENER IN TISSUE

[75] Inventors: Gene W. Kammerer, E. Brunswick; Jack S. Pedlick, Butler; Keith A. Seritella, Kendall Park, all of N.J.

[73] Assignee: Mitek Surgical Products, Inc., Westwood, Mass.

[21] Appl. No.: 08/856,102

[22] Filed: May 14, 1997

[51] Int. Cl.⁶ .................................................. A43D 69/00
[52] U.S. Cl. ........................................... 227/67; 227/175.1
[58] Field of Search .................................. 227/67, 68, 71, 227/175.1, 179.1, 19

[56] References Cited

U.S. PATENT DOCUMENTS

| | | | |
|---|---|---|---|
| 4,006,747 | 2/1977 | Kronenthal et al. | 128/335 |
| 4,235,238 | 11/1980 | Ogiu et al. | 128/334 R |
| 4,333,596 | 6/1982 | Kunreuther | 227/68 |
| 4,438,769 | 3/1984 | Pratt et al. | 227/175.1 |
| 4,448,194 | 5/1984 | DiGiovanni et al. | 227/67 |
| 4,669,473 | 6/1987 | Richards et al. | 128/334 |
| 4,705,040 | 11/1987 | Mueller et al. | 128/334 R |
| 5,152,749 | 10/1992 | Giesy et al. | 604/164 |
| 5,289,963 | 3/1994 | McGarry et al. | 227/175.1 |
| 5,489,057 | 2/1996 | Deschenes | 227/67 |
| 5,588,575 | 12/1996 | Davignon | 227/67 |
| 5,601,571 | 2/1997 | Moss | 606/139 |
| 5,632,432 | 5/1997 | Schulze et al. | 227/176.1 |
| 5,697,542 | 12/1997 | Knodal et al. | 227/175.1 |
| 5,715,984 | 2/1998 | Deschenes | 227/67 |

*Primary Examiner*—Jessica J. Harrison
*Assistant Examiner*—John Paradiso
*Attorney, Agent, or Firm*—Pandiscio & Pandiscio

[57] ABSTRACT

An applicator for deploying a fastener into tissue, the fastener including a head portion and a filament portion extending from the head portion, the applicator comprising an elongated hollow needle member having a pointed distal end portion, a slotted portion for releasably retaining the head of the shaped fastener, and a first connector portion; and a chuck comprising a second connector portion engageable with the first connector portion for interconnecting the needle member and the chuck, a push rod having a distal end portion adapted to move lengthwise in the needle member, and an actuator for moving the push rod in the needle member so as to eject the head portion of the fastener from the slotted portion of the needle member. A method for deploying the fastener in tissue is also disclosed.

16 Claims, 18 Drawing Sheets

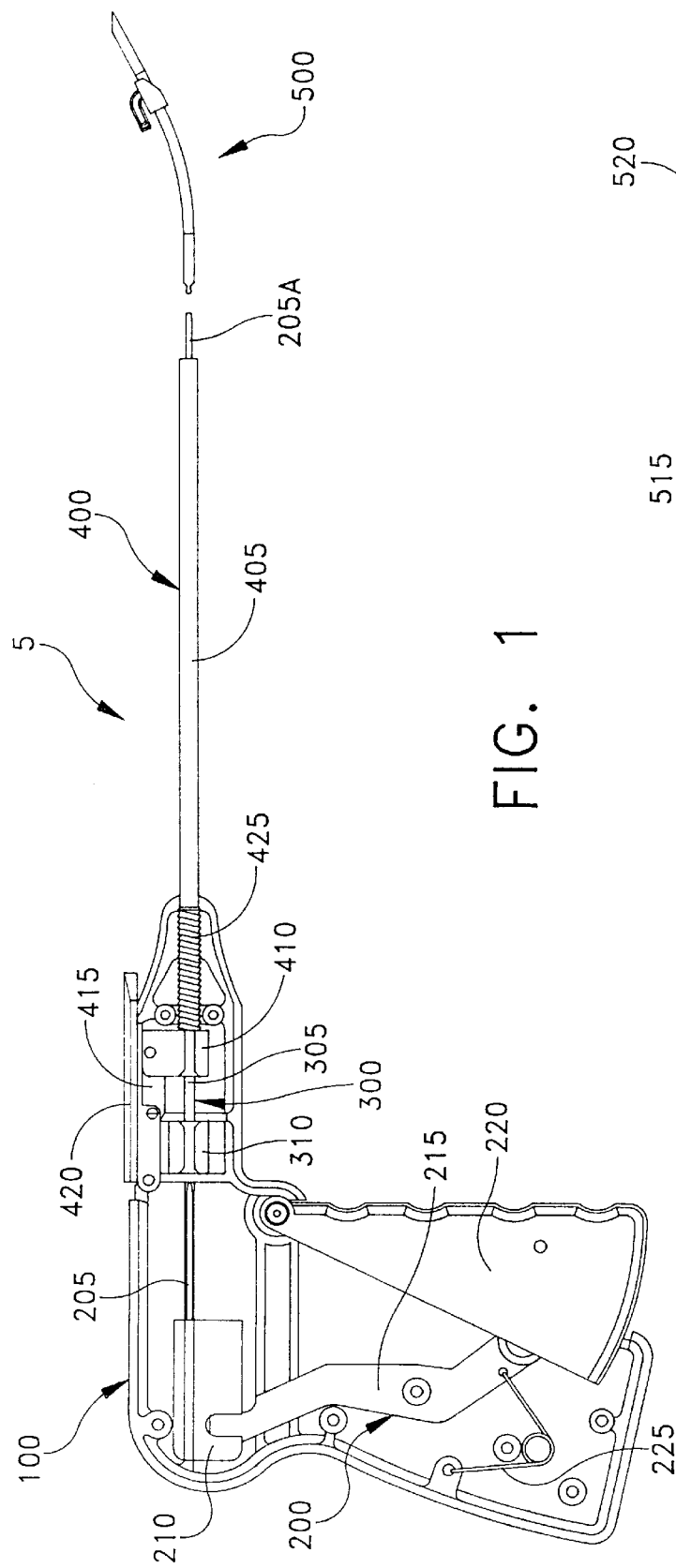
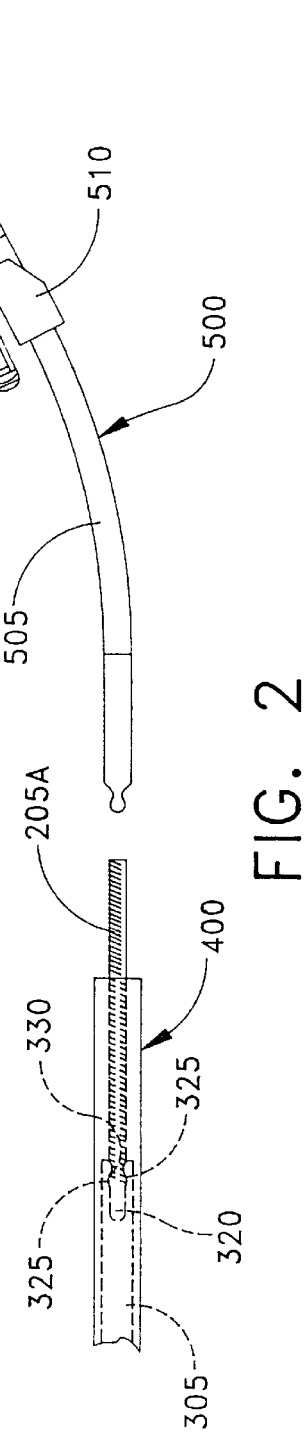
FIG. 1
FIG. 2

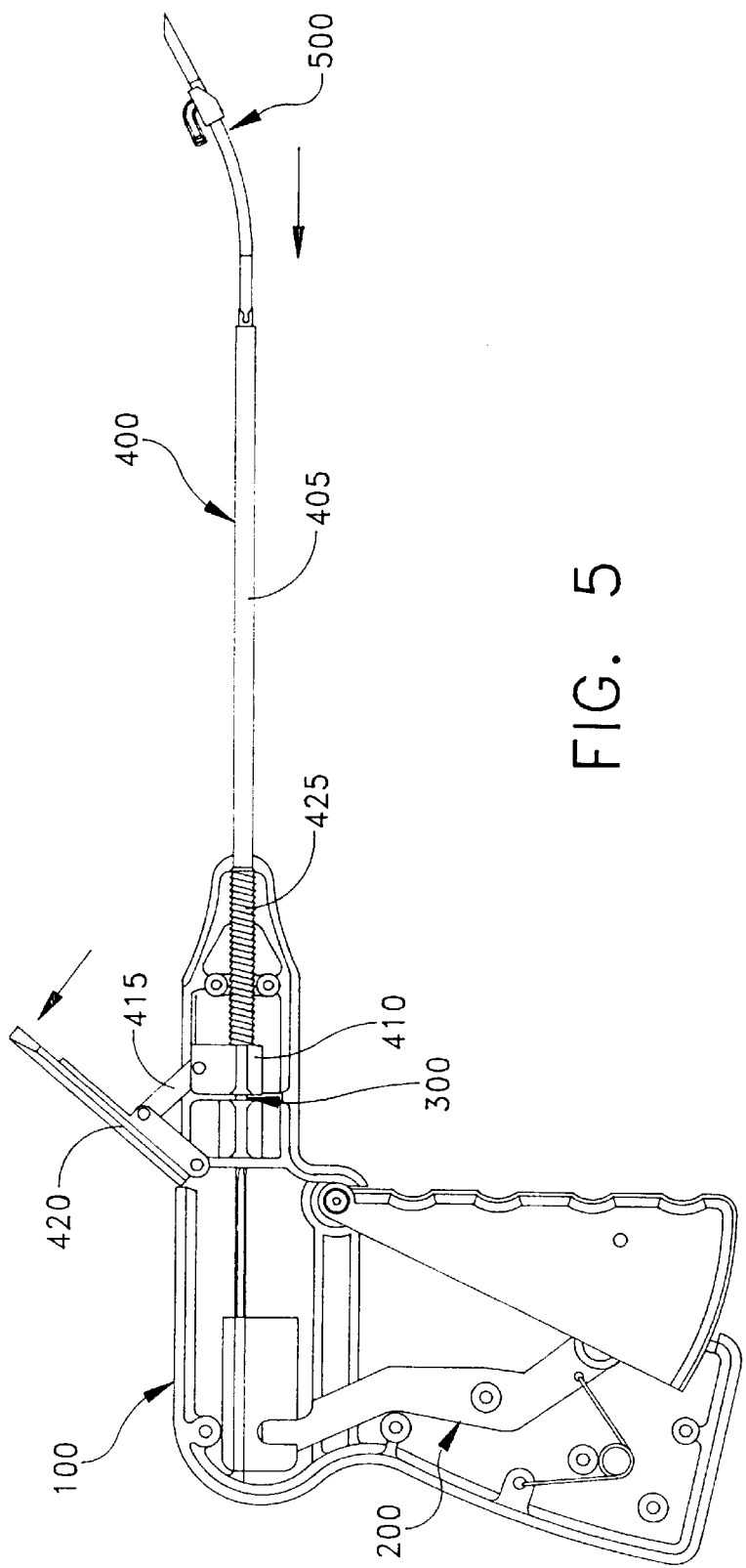
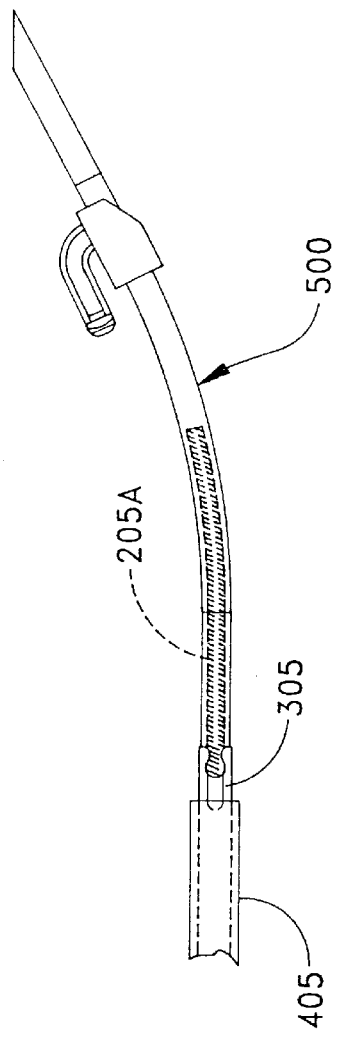
FIG. 5
FIG. 6

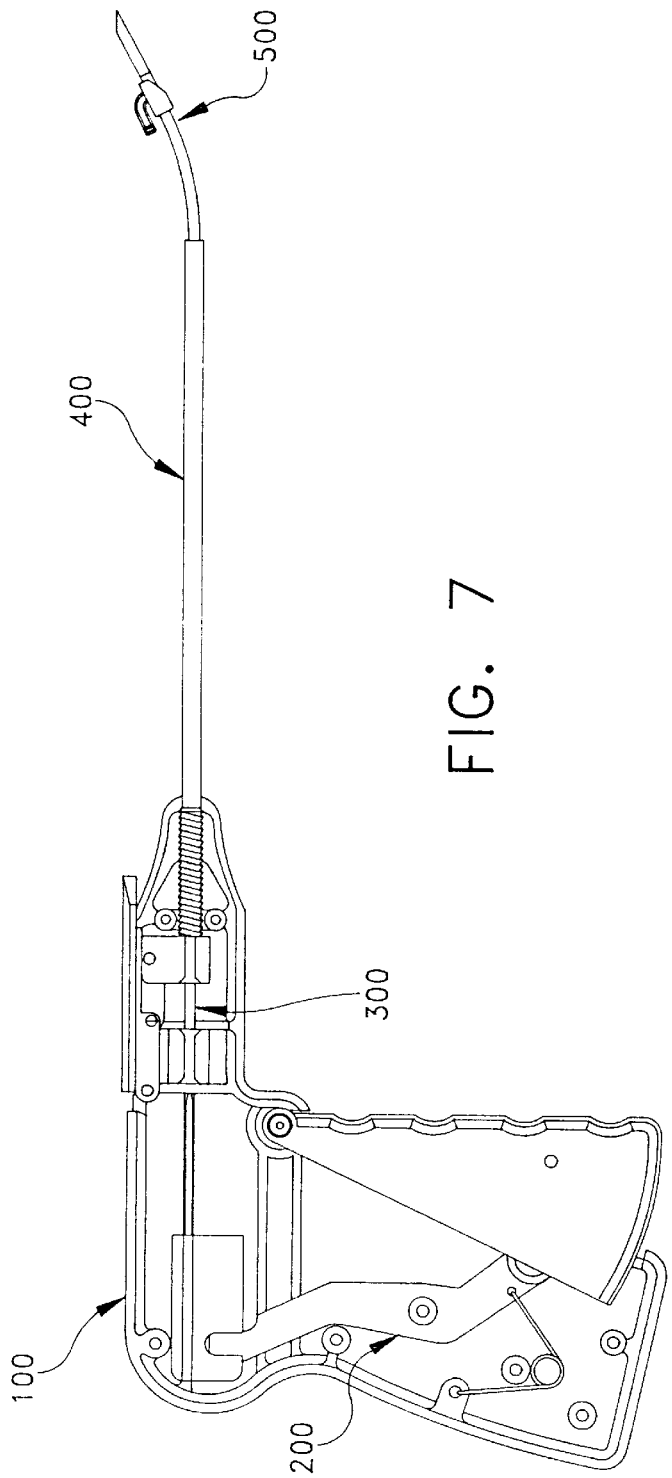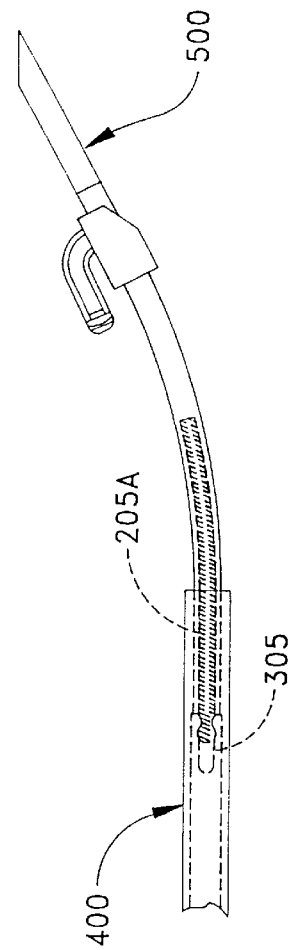

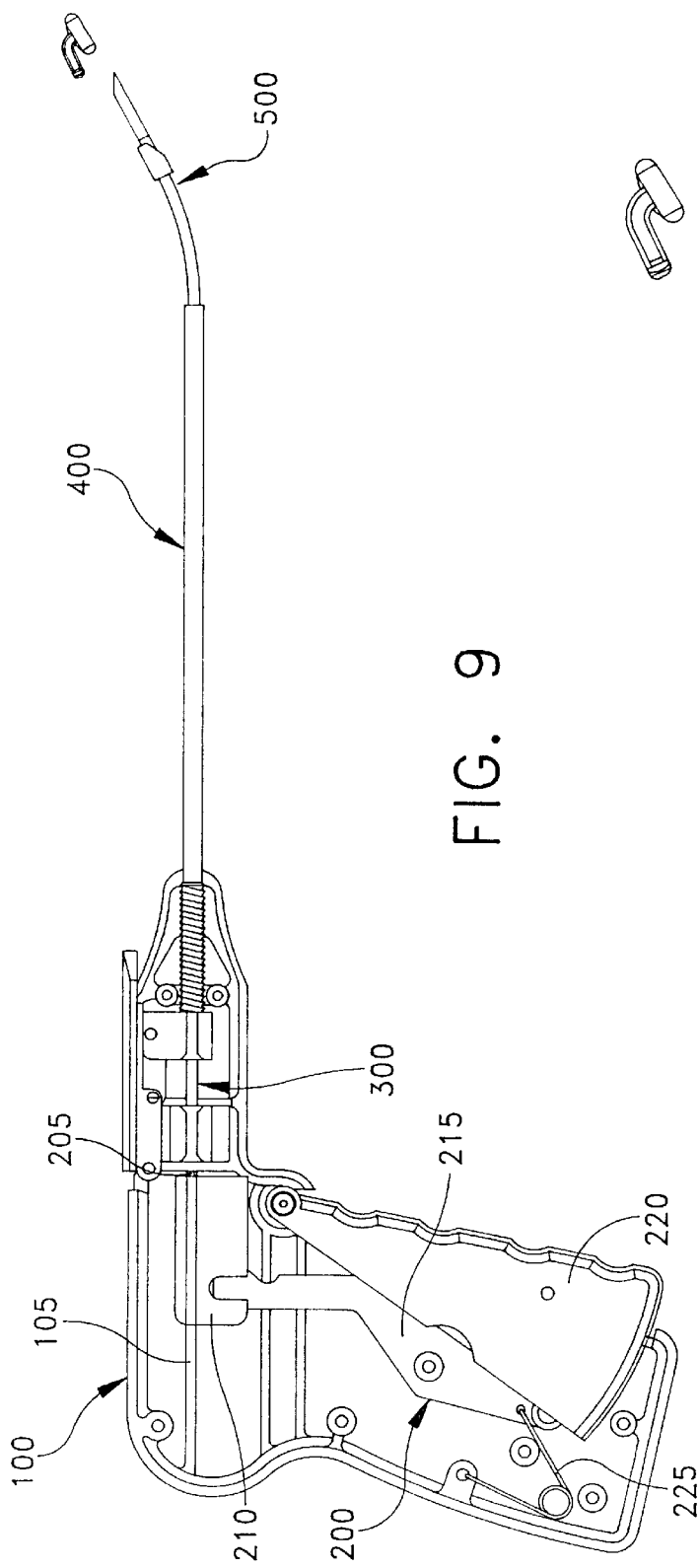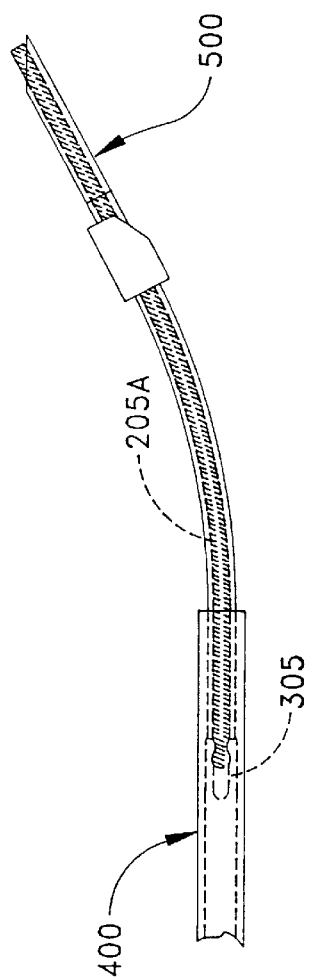

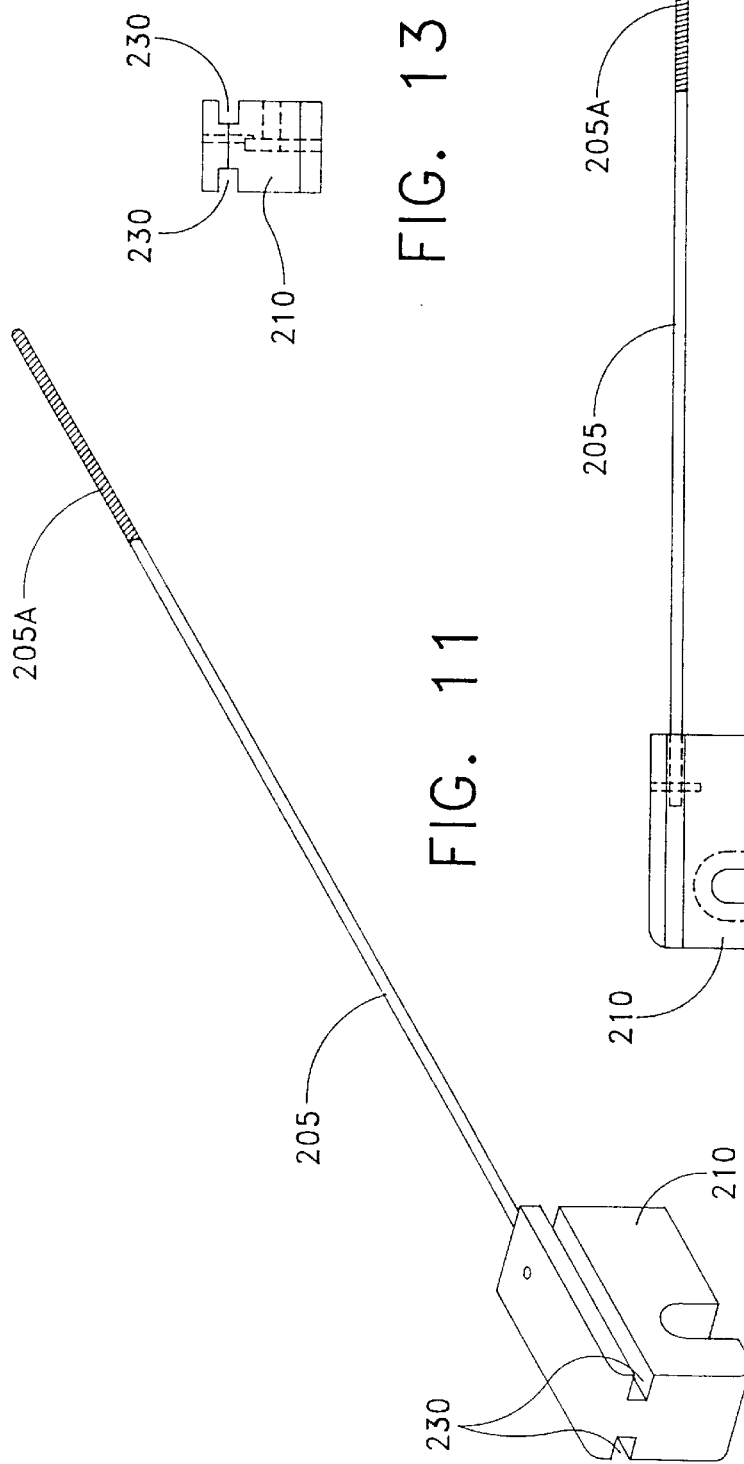

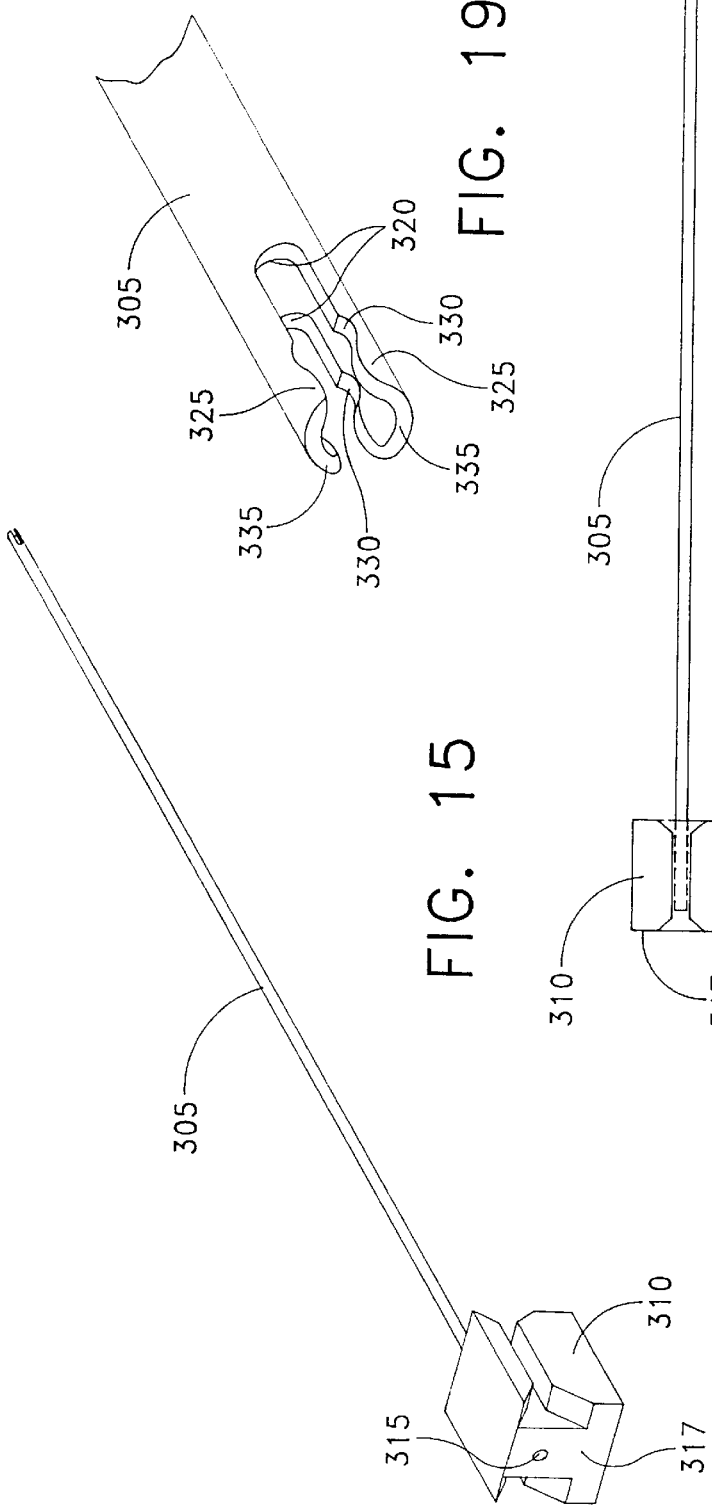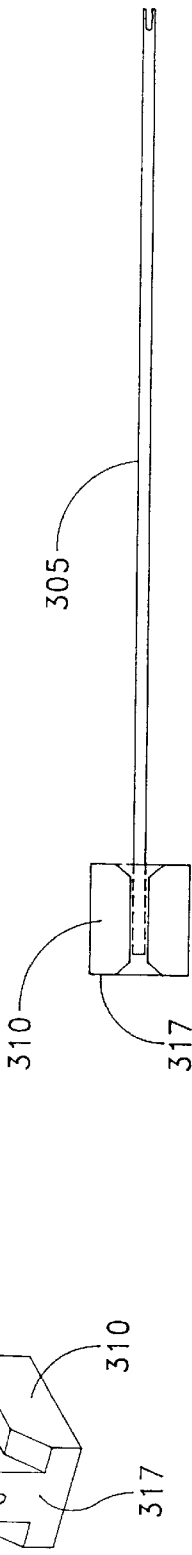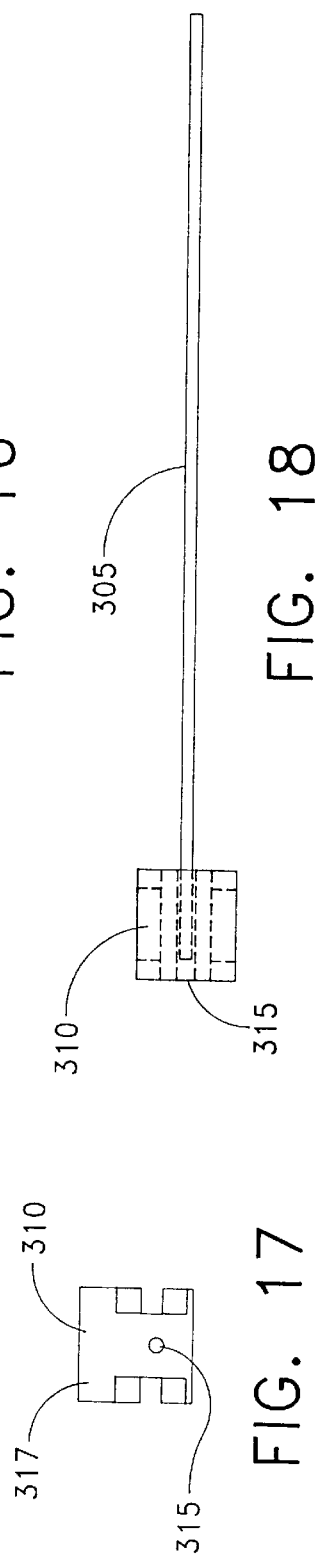

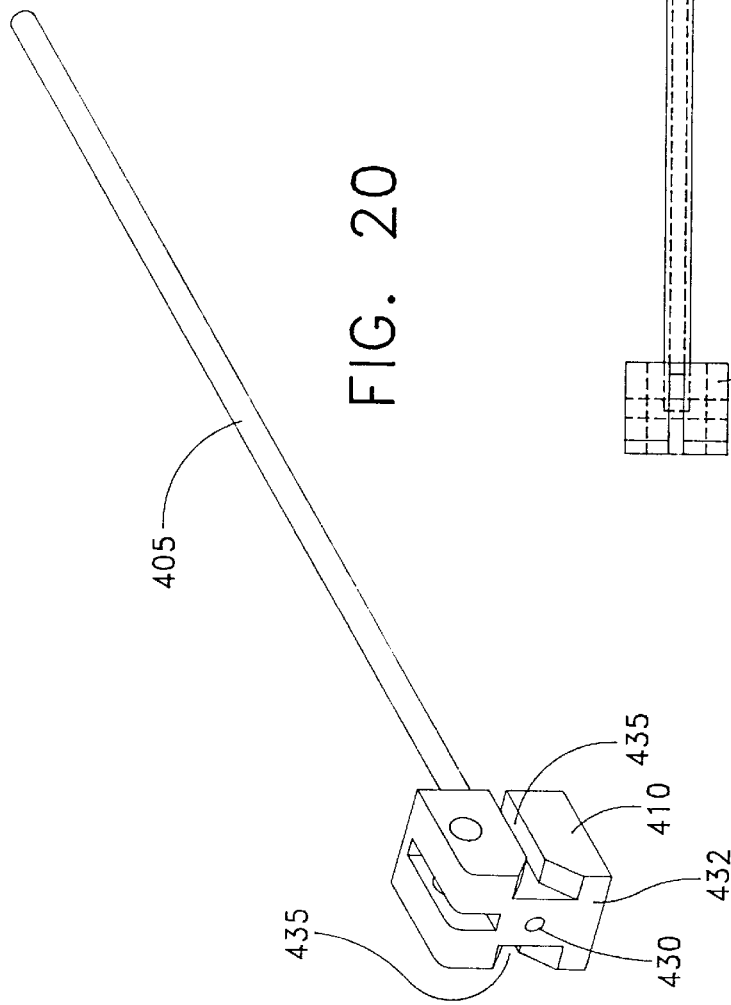
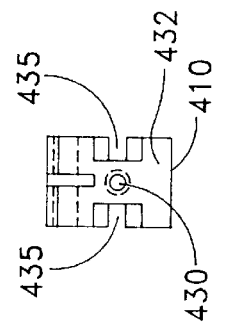
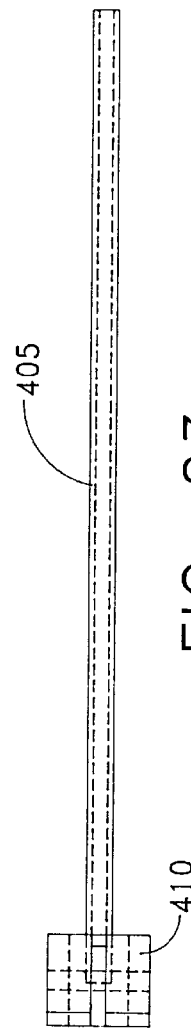
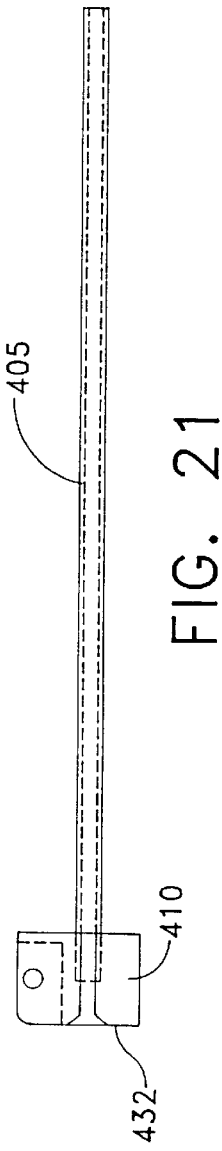

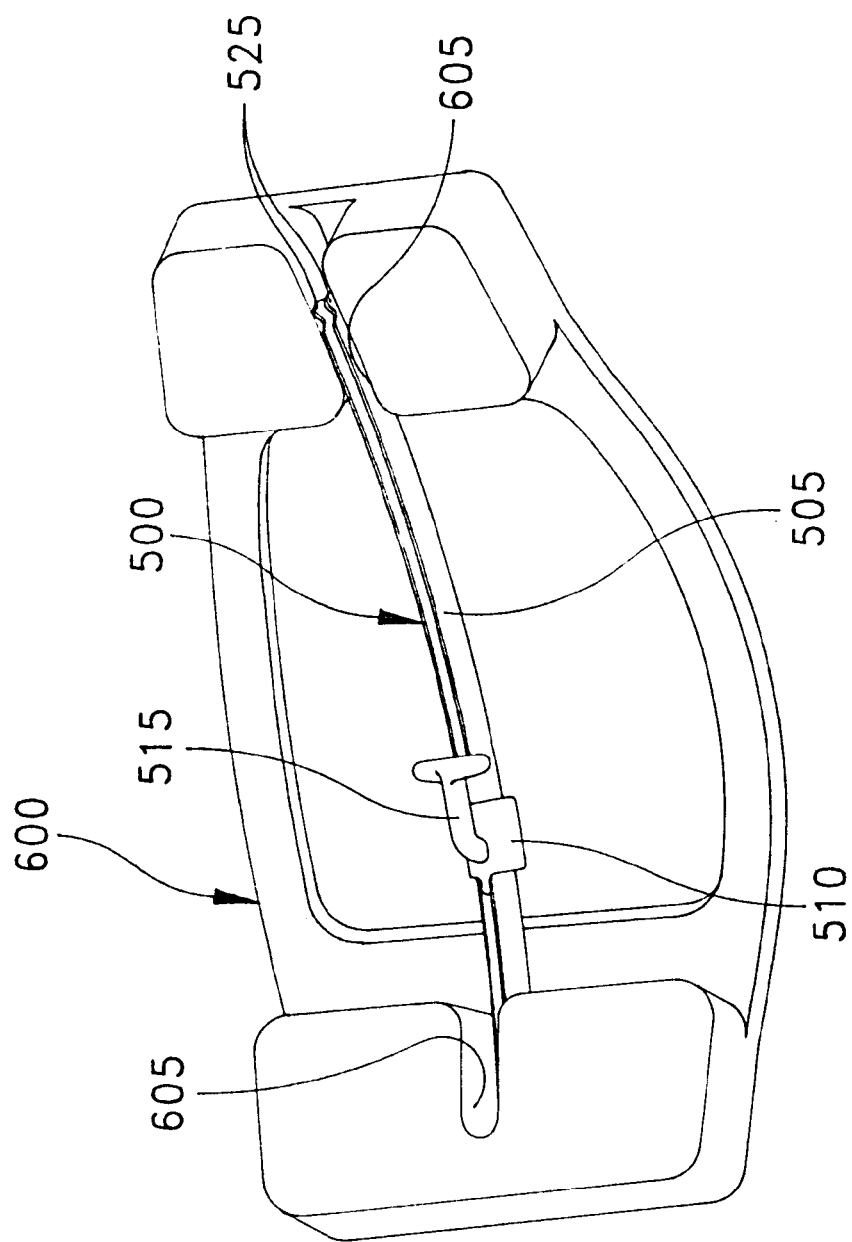

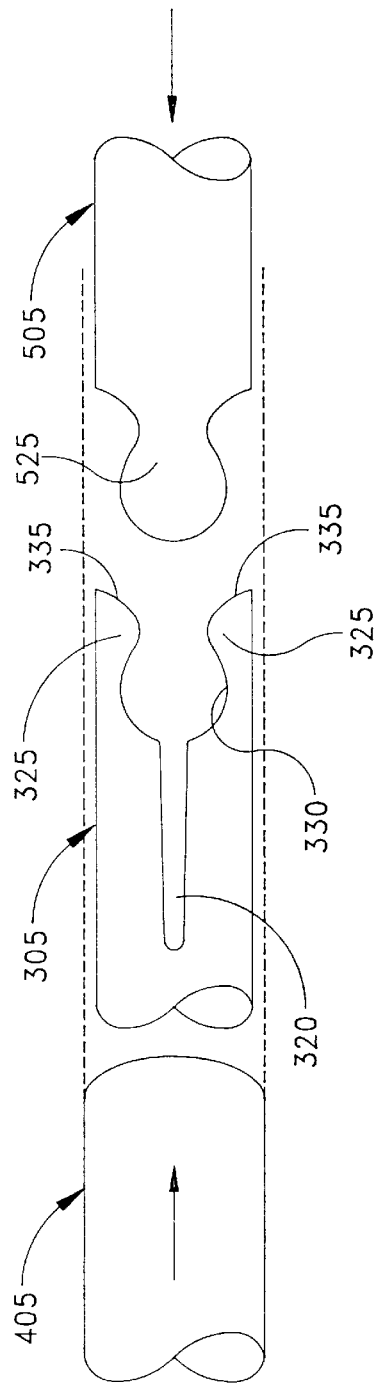
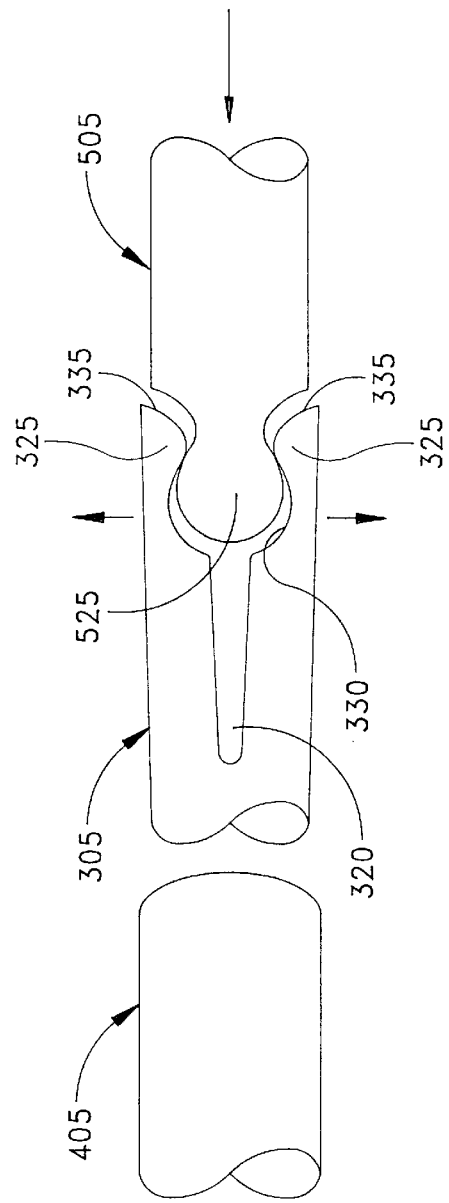
FIG. 34
FIG. 35

APPLICATOR AND METHOD FOR DEPLOYING A SURGICAL FASTENER IN TISSUE

FIELD OF THE INVENTION

This invention relates to surgical apparatus and procedures in general, and more particularly to applicators and methods for deploying surgical fasteners in tissue.

BACKGROUND OF THE INVENTION

In many situations, one piece of tissue must be attached to another piece of tissue.

For example, an open wound or surgical incision may need to be closed. Or an injury may cause one piece of tissue (e.g., a tendon) to become detached from another piece of tissue (e.g., a bone). Or a piece of tissue (e.g., a piece of meniscal cartilage) may tear in its midst.

The traditional technique for attaching one piece of soft tissue to another piece of soft tissue has involved stitching the two pieces of tissue together using suture. However, in many circumstances such stitching can be problematic, either because of the time required to do the stitching, or the difficulty of stitching in a particular area of the body, etc.

More recently, different types of surgical fasteners have been developed for holding together two pieces of tissue. Among the fasteners which have been developed to date is the so-called T-type fastener, in which a rod-like head is perpendicularly mounted to the end of a length of flexible filament. Another of these fasteners is the so-called H-type fastener, in which rod-like heads are perpendicularly mounted to the two opposite ends of an intermediate, bridging flexible filament.

Appropriate applicator tools have also been developed for deploying such fasteners in tissue.

Examples of such T-type and H-type fasteners, and their associated applicators, are disclosed in U.S. Pat. Nos. 4,006,747 (Kronenthal et al.); U.S. Pat. No. 4,235,238 (Ogiu et al.); U.S. Pat. No. 4,669,473 (Richards et al.); and U.S. Pat. No. 4,705,040 (Mueller et al.).

Unfortunately, applicators for deploying such T-type and H-type fasteners in tissue have not been completely satisfactory to date, for a variety of reasons.

OBJECTS OF THE INVENTION

As a result, one object of the present invention is to provide an improved applicator for deploying T-type and H-type fasteners in tissue.

Another object of the present invention is to provide an improved method for deploying T-type and H-type fasteners in tissue.

SUMMARY OF THE INVENTION

These and other objects are addressed by the present invention, which comprises an improved applicator and method for deploying T-type and H-type fasteners in tissue.

In a preferred form of the invention, the applicator for deploying T-type and H-type fasteners in tissue comprises an elongated hollow needle member having a pointed distal end portion, a slotted portion for releasably retaining the head of the shaped fastener, and a first connector portion; and a chuck comprising a second connector portion engageable with the first connector portion for interconnecting the needle member and the chuck, a push rod having a distal end portion adapted to move lengthwise in the needle member, and an actuator for moving the push rod in the needle member so as to eject the head portion of the fastener from the slotted portion of the needle member.

In a preferred form of the invention, the method for deploying T-type and H-type fasteners in tissue comprises the steps of: placing a head portion of the fastener within a slotted portion of a hollow needle member; attaching the needle member to a chuck extending from a tool; manipulating the tool to slide a sleeve over an attachment juncture of the needle member and the chuck so as to lock the needle member in the chuck; advancing the needle member within the body to a point wherein the needle member slotted portion is adjacent to an area in which placement of the fastener is desired; and manipulating the tool to move a push rod centrally of the chuck so as to engage the fastener and eject the head portion of the fastener from the slotted portion of the needle member.

BRIEF DESCRIPTION OF THE DRAWINGS

These and other objects and features of the present invention will be more fully disclosed or rendered obvious by the following detailed description of the preferred embodiment of the invention, which is to be considered together with the accompanying drawings wherein like numbers refer to like parts, and further wherein:

FIG. 1 is a side view of an applicator formed in accordance with the present invention, with the applicator being shown in a first operating position;

FIG. 2 is a enlarged side view of the distal end of the applicator shown in FIG. 1;

FIG. 5 is a side view of the applicator of FIG. 1, with the applicator being shown in a third operating position;

FIG. 6 is a enlarged side view of the distal end of the applicator shown in FIG. 5;

FIG. 7 is a side view of the applicator of FIG. 1, with the applicator being shown in a fourth operating position;

FIG. 8 is a enlarged side view of the distal end of the applicator shown in FIG. 7;

FIG. 9 is a side view of the applicator of FIG. 1, with the applicator being shown in a fifth operating position;

FIG. 10 is a enlarged side view of the distal end of the applicator shown in FIG. 9;

FIGS. 11–14 are views showing construction details of selected portions of the applicator's push rod assembly;

FIGS. 15–19 are views showing construction details of selected portions of the applicator's chuck assembly;

FIGS. 20–23 are views showing construction details of selected portions of the applicator's sleeve assembly;

FIG. 29 is a perspective view showing a tray for holding the applicator's needle assembly prior to joinder of the needle assembly with the remainder of the applicator;

FIGS. 30–40 are schematic views showing various steps in the use of the applicator in an exemplary tissue repair application;

DETAILED DESCRIPTION OF THE PREFERRED EMBODIMENT

Figure 3:
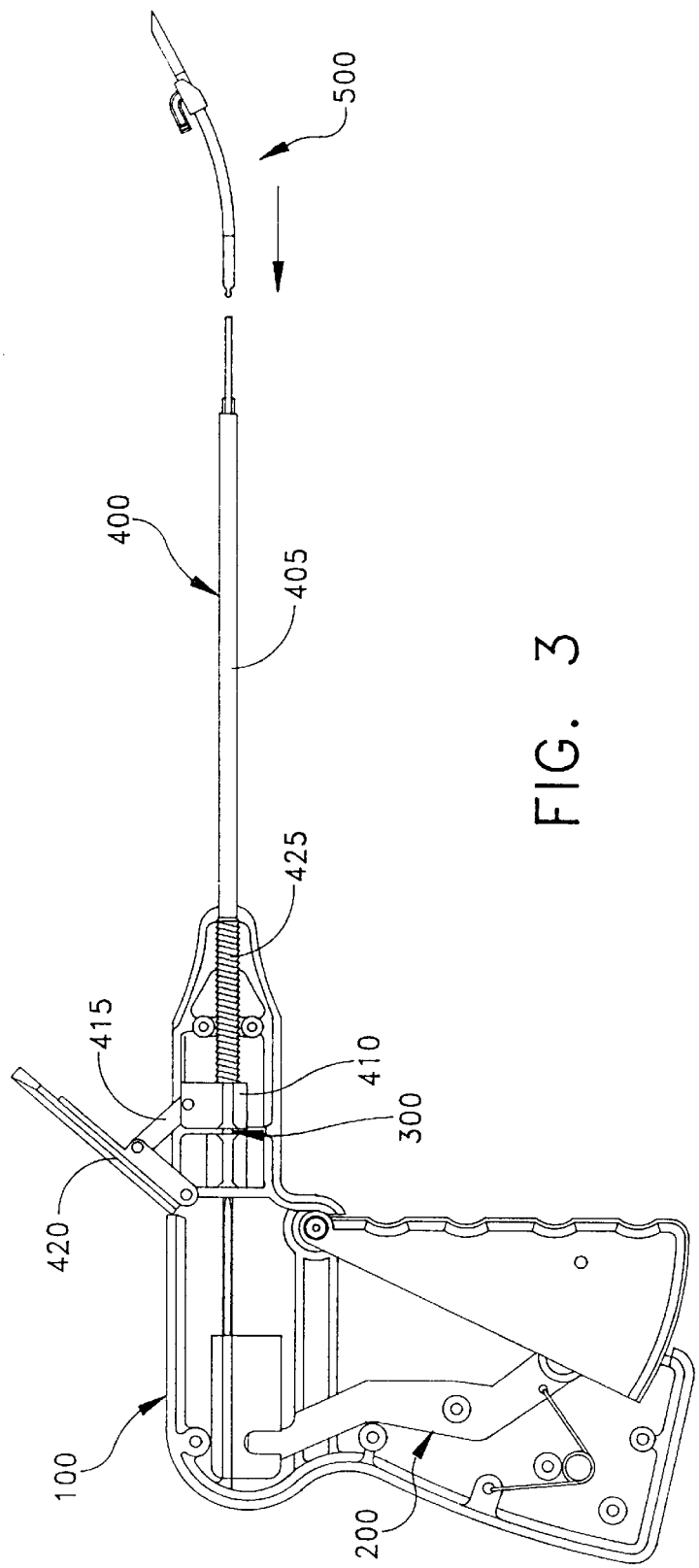
FIG. 3 is a side view of the applicator of FIG. 1, with the applicator being shown in a second operating position.

Looking first at FIGS. 1 and 2, there is shown an applicator 5 formed in accordance with the present invention. Applicator 5 generally comprises a housing 100, a push rod assembly 200, a chuck assembly 300, a sleeve assembly 400, and a needle assembly 500.

Housing 100 is preferably formed in the shape of a pistol grip so as to easily conform to the hand of a user. Housing 100 serves to provide a support structure for the remainder of the elements of the applicator, as will hereinafter be described in further detail. Housing 100 is preferably formed as two mirror halves (only one of which is shown in FIG. 1) so as to simplify manufacture of the applicator, with the two halves being joined during assembly so as to form the complete housing structure.

Looking next at FIGS. 1, 2 and 11–14, push rod assembly 200 generally comprises a push rod 205, a slide block (or sled) 210, a pivot lever 215, a trigger 220, and a spring 225. The proximal end of push rod 205 is preferably solid, and it is secured to slide block 210 so that push rod 205 will move in unison with slide block 210. The distal end of push rod 205 preferably comprises a flexible but relatively incompressible spring 205A, whereby the distal end of the push rod can follow the curvature of needle assembly 500, as will hereinafter be discussed in further detail. Pivot lever 215 and trigger 220 are pivotally mounted to housing 100, whereby (i) when trigger 220 is in its forward position (FIG. 1), slide block 210 and push rod 205 will be in their rearward positions (FIGS. 1 and 2), and (ii) when trigger 220 is in its rearward position (FIG. 9), slide block 210 and push rod 205 will be in their forward positions (FIGS. 9 and 10). Spring 225 yieldably biases trigger 220 into its forward position, and hence slide block 210 and push rod 205 into their rearward positions (FIG. 1). If desired, slide block 210 may be formed with side groves 230 (FIGS. 11 and 13) for riding on side rails 105 (FIG. 9) formed on housing 100, whereby slide block 210 can be further stabilized as it moves within the housing.

Looking next at FIGS. 1, 2 and 15–19, chuck assembly 300 comprises a tubular chuck 305 and a block 310. The proximal end of chuck 305 is secured to block 310, and block 310 is in turn secured to housing 100, whereby chuck 305 will be secured to housing 100. An opening 315 in block 310 communicates between the proximal end surface 317 of block 310 and the hollow interior of chuck 305. The distal end of chuck 305 comprises a pair of diametrically-opposed slots 320 (FIGS. 2 and 19) which together define a pair of arms 325. Arms 325 are constructed so that they can flex outwardly slightly upon appropriate urging, as will hereinafter be discussed in further detail. Each of the slots 320 has a keyway geometry, such that it includes an enlarged opening 330 intermediate its length. The distal end surfaces 335 of arms 325 are beveled, for reasons which will hereinafter be discussed. Chuck assembly 300 is sized and positioned so that it will slidingly receive push rod 205. Chuck assembly 300 is also sized so that push rod 205 will extend out of the distal end of chuck 305 regardless of whether the push rod is in its retracted position (FIGS. 1 and 2) or its projected position (FIGS. 9 and 10).

Looking next at FIGS. 1, 2 and 20–23, sleeve assembly 400 generally comprises a sleeve 405, a slide block (or sled) 410, a pivot arm 415, a lock lever 420, and a spring 425. The proximal end of sleeve 405 is secured to slide block 410, whereby sleeve 405 will move in unison with slide block 410. An opening 430 in slide block 410 communicates between the proximal end surface 432 of block 410 and the hollow interior of sleeve 405. Sleeve 405 and slide block 410 are sized and positioned so that they will receive, and slidingly ride on, chuck 305. Pivot arm 415 extends between, and is pivotally connected to, slide block 410 and lock lever 420. Lock lever 420 is in turn pivotally connected to housing 100, whereby (i) when lock lever 420 is in its down position (FIG. 1), slide block 410 and sleeve 405 will be in their forward positions (FIGS. 1 and 2), whereupon sleeve 405 will engulf the distal end of chuck 305, and (ii) when lock lever 420 is in its up position (FIG. 3), slide block 410 and sleeve 405 will be in their rearward positions (FIGS. 3 and 4), whereupon the distal end of chuck 305 will project out of the distal end of sleeve 405. Spring 425 helps move slide block 410 and sleeve 405 into their rearward positions once these elements begin to move from their forward positions (FIG. 1) to their rearward positions (FIG. 3). If desired, slide block 410 may be formed with side grooves 435 (FIGS. 20 and 22) for riding on corresponding side rails (not shown) formed on housing 100, whereby slide block 210 can be further stabilized as it moves within the housing.

Looking next at FIGS. 1, 2 and 24–28, needle assembly 500 comprises a hollow needle 505, a collar 510, and a fastener 515.

Needle 505 is generally curved along its length (FIG. 2). The specific degree of curvature will depend on the medical procedure to be accomplished; thus, it is intended that a particular needle assembly 500 will be selected by the user from a set of different needle assemblies 500 made available to the user prior to the start of the procedure. The distal end of needle 505 terminates in a sharp point 520. The proximal end of needle 505 has a diameter which is substantially the same as the diameter of chuck 305. The proximal end of needle 505 terminates in a pair of diametrically-opposed tabs 525. Tabs 525 have a configuration which mirrors the configuration of the chuck's slots 320, for reasons which will hereinafter be discussed in further detail. A slot 530 extends along the length of needle 505 and communicates with the interior of the hollow needle. Preferably slot 530 extends along substantially the entire length of needle 505; however, if desired, slot 530 could be formed in only the distal portion of needle 505, and slot 530 could be omitted from the proximal portion of the needle.

Figure 27:
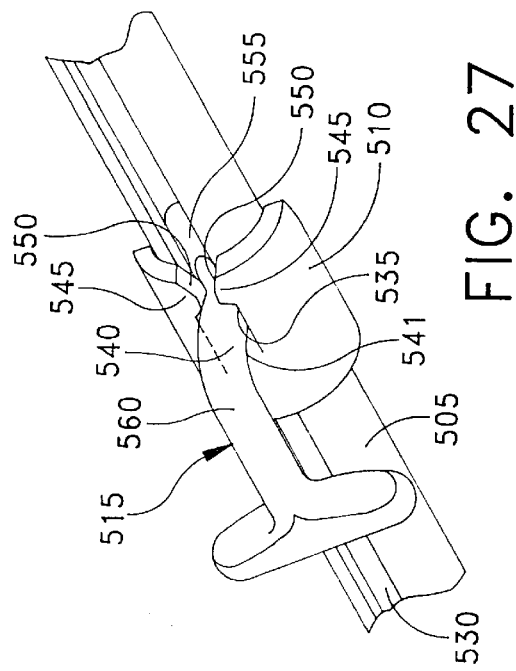
Figure 24:
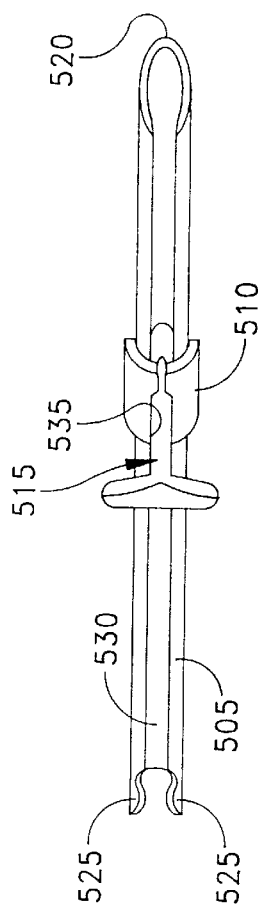
Figure 26:
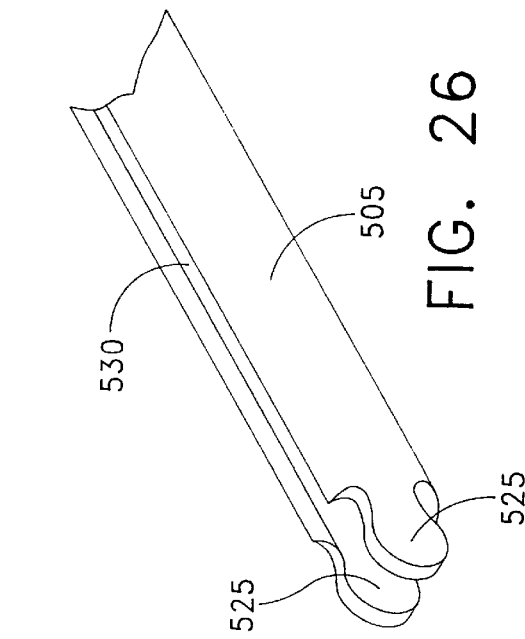

Collar 510 is mounted on needle 505. A slot 535 (FIGS. 24 and 27) is formed in collar 510. Slot 535 opens on the distal end of collar 510 and terminates intermediate the length of the collar in a surface 540. Preferably surface 540 is formed by bending a portion of the top surface of collar 510 downward so as to form a sort of sloping tab 541 (FIG. 27). A pair of fingers 545 extend into the collar's slot 535, on the distal side of proximal surface 540. The distal ends 550 of fingers 545 have a beveled configuration.

Needle 505 is sized so as to slidably receive a head 555 of fastener 515 (FIGS. 27 and 28), while permitting a filament 560 of the fastener to slidably extend through the needle's slot 530 and the collar's slot 535, with the filament resting on sloping tab 541. Collar fingers 545 releasably hold filament 560, and hence fastener 515, in place on the needle.

Figure 28:
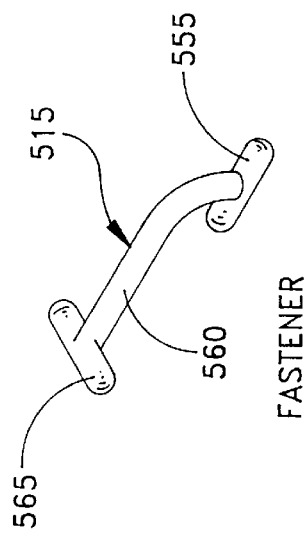
FIG. 28 is a perspective view showing one type of fastener which can be used in conjunction with the present invention.

More particularly, fastener 515 is preferably an H-type fastener of the sort comprising a first head 515, a second head 565, and a connecting flexible filament 560 (FIG. 28). The composition of fastener 515 will depend on the medical procedure to be accomplished, e.g., for some applications fastener 515 might be formed out of polydioxanone so as to be absorbable, or in some applications fastener 515 may be formed out of a non-absorbable material such as polypropylene. Furthermore, the length of filament 560 will also depend on the particular procedure to be conducted. It is intended that the proper fastener composition and length will be selected by the user from a set of different, pre-loaded needle assemblies 500 made available to the user prior to the start of the procedure. Fastener 515 is sized so that its head 555 can be slid along the hollow interior of needle 505, while the fastener's flexible filament 560 extends out through the needle's slot 530. Collar 510 is sized so that the fastener's filament 560 can slip past the collar's beveled surfaces 550 and thereafter be releasably captured in the collar's slot, between the collar's fingers 545 and the collar's proximal surface 540. Such releasable capture helps hold fastener 515 in position on needle 505 during delivery to the surgical site, yet allows the fastener to separate from the needle under appropriate urging, as will hereinafter be discussed in further detail.

It should also be appreciated that collar 510 also serves as an appropriate stop to limit penetration of needle 505 into the tissue during fastener deployment. In addition, collar 510 also serves to provide compression to the tissue during placement of the fastener, so as to assure good approximation of tissue edges.

Looking next at FIG. 29, needle assembly 505 is preferably pre-packaged in a tray 600. Tray 600 comprises a slot 605 for receiving the needle assembly. The distal end of slot 605 is preferably closed off, or otherwise arranged, whereby the sharp point 520 of needle 505 will be shielded against accidental contact by the user. The proximal end of slot 605 is preferably open, or otherwise arranged, whereby the needle's two tabs 525 will be exposed for engagement by the distal end of chuck 305, as will hereinafter be discussed in further detail. Preferably tray 600 is formed so as to provide the proximal end of slot 605 with a funnel-like configuration, so as to facilitate mating of chuck 305 with needle 505. Needle assembly 500 and tray 600 are preferably pre-packaged in a sterilized blister pack which can be opened at the time of use.

Operation of applicator 5 will now be described. By way of example but not limitation, the operation of applicator 5 will be discussed in the context of using fastener 515 to close a tear in a piece of meniscal tissue, although many other applications of the present invention will be readily apparent to those skilled in the art.

Figure 30:
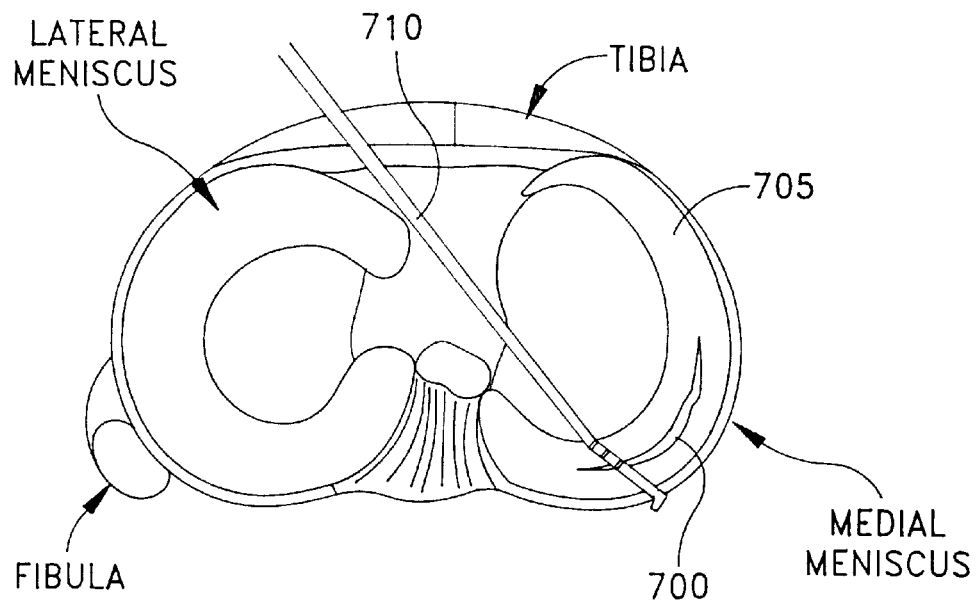
Figure 31:
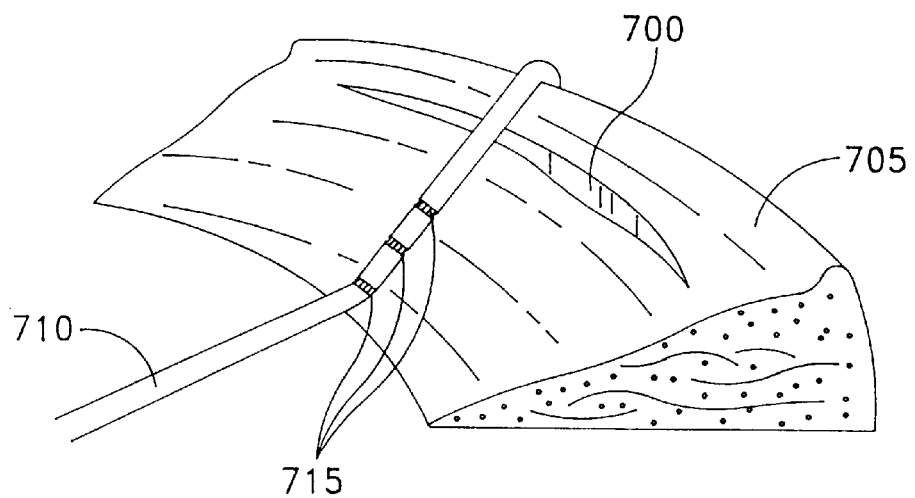
Figure 32:
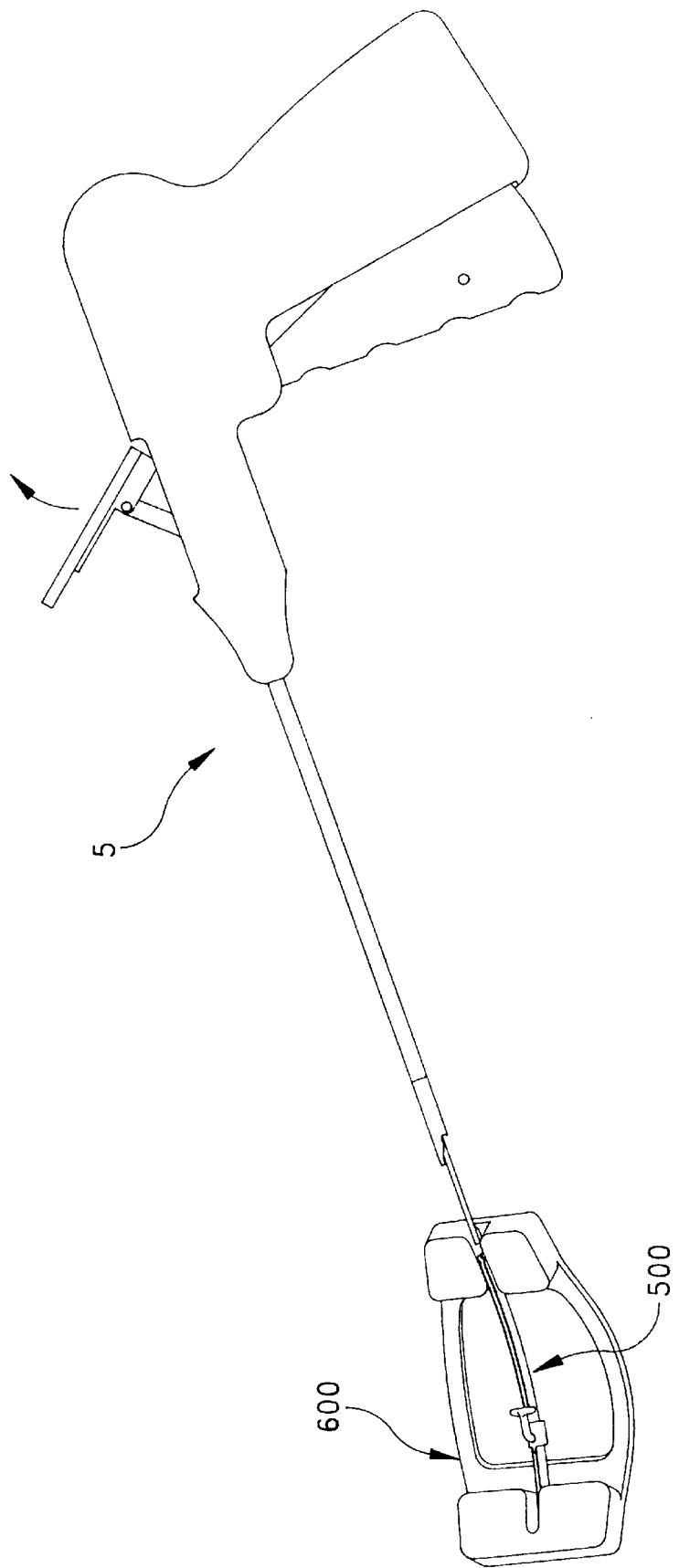
Figure 33:
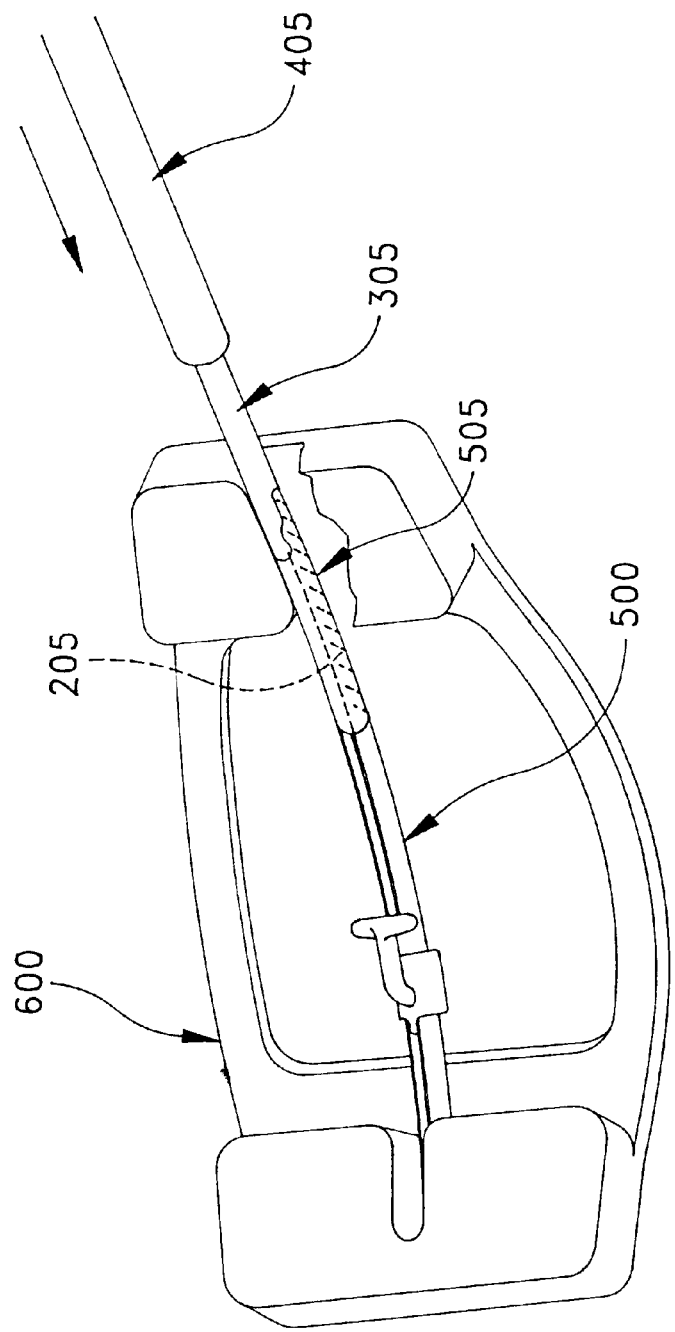

Looking next at FIG. 30, the tear 700 in the meniscus 705 is first inspected so as to determine the proper length of fastener to be used. More particularly, a probe 710 is preferably extended across the meniscus and, using markings 715 (FIG. 31) thereon, the location and size of the tear is determined. This information is then used to identify the proper length of fastener to be used to effect the desired repair.

The user also determines the type of fastener which is to be used (e.g., polydioxanone or polypropylene composition), and the preferred needle configuration (e.g., the degree of curvature). A pre-packaged needle assembly 500 which meets these determined criteria is then selected by the user from an assortment of different, pre-packaged needle assemblies.

Once the desired needle package has been selected, the user opens the needle package using routine aseptic techniques so as to expose the desired needle assembly 500, which is disposed in its associated tray 600 (FIG. 29).

Figure 4:
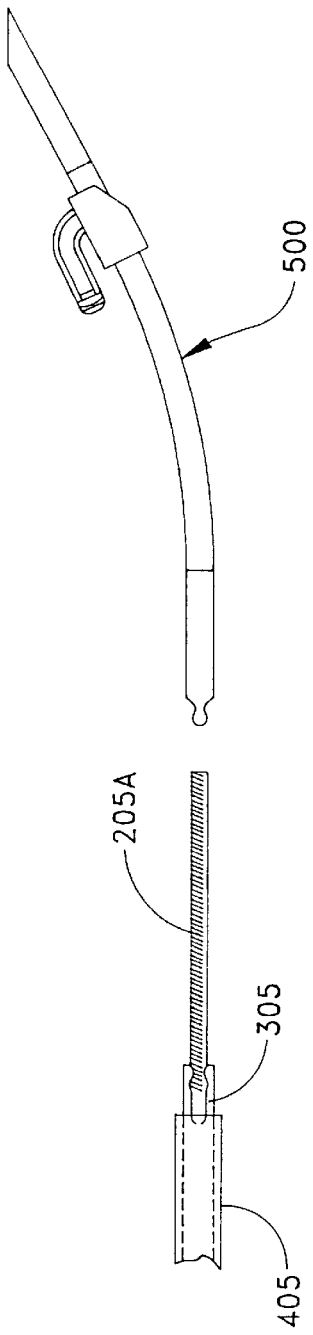
FIG. 4 is a enlarged side view of the distal end of the applicator shown in FIG. 3.
Figure 25:
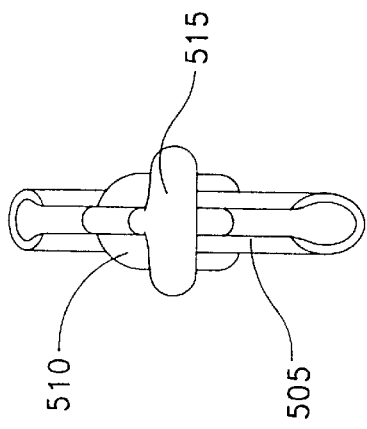
FIGS. 24–27 are views showing construction details of selected portions of the applicator's needle assembly.

Next, the user prepares applicator 5 to pick up needle assembly 500. More particularly, the user picks up applicator 5, which is normally in the configuration shown in FIGS. 1 and 2 (i.e., with trigger 220 out and lock lever 420 down). The user then readies applicator 5 to receive needle assembly 500, by lifting lock lever 420 upward (FIGS. 3 and 4). This causes sleeve 405 to be retracted so as to expose the distal tip of chuck 305.

Figure 36:
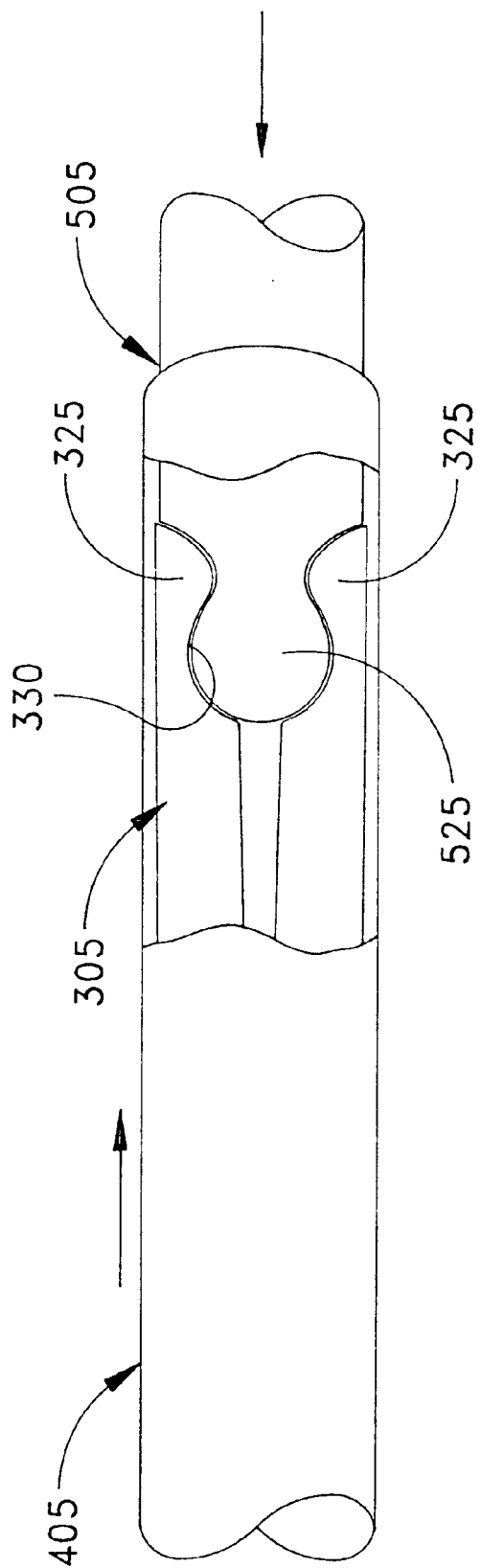

Next, the distal end of applicator 5 is passed into the funnel end of tray 600 so that the distal end of the applicator engages the proximal end of needle assembly 500 (FIGS. 5, 6, 32 and 33). As this occurs, the distal end of push rod 205 first slips within the needle's hollow interior, and then the distal end of chuck 305 engages the needle's two tabs 525. As shown in FIGS. 34 and 35, the initial engagement of the chuck's beveled surfaces 335 with the needle's tabs 525 causes the chuck's two arms 325 to flex outward slightly, such that the tabs 325 can slip into, and seat within, the chuck's keyway slots 320. Then lock lever 420 is lowered again so as to move the distal end of sleeve 405 forward, over the union of needle 505 and chuck 305 (FIGS. 7, 8 and 36). This action makes needle assembly 500 fast to applicator 5, by ensuring that the chuck's arms 325 cannot flex open again so as to release needle assembly 500. In this respect it will be appreciated that (i) sleeve 405 is constructed so that it has an inside diameter which is just slightly larger than the outer diameter of chuck 305 and needle 505; and (ii) the clearance between chuck 305 and tube 405 is such that it is smaller than the distance required for the chuck to open in order to release the needle, and the clearance is smaller than the distance required for the needle to move sideways so as to separate from the chuck.

At this point needle assembly 500 is withdrawn from tray 600 using applicator 5.

Figure 38:
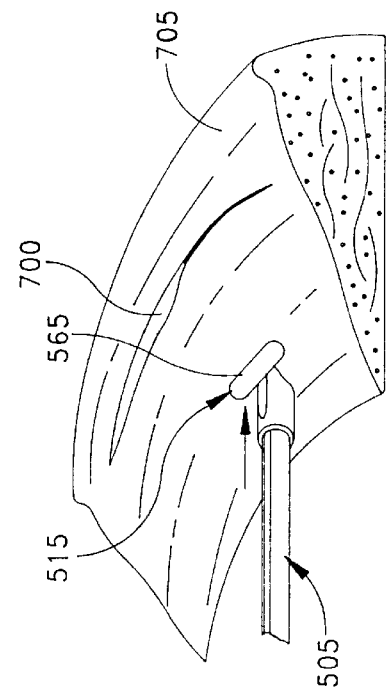
Figure 37:
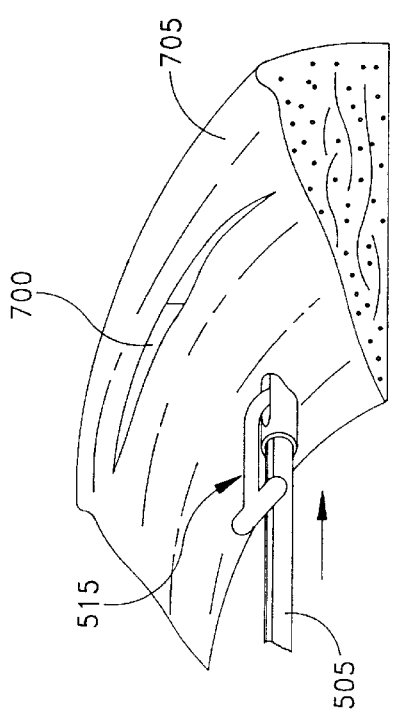
Figure 40:
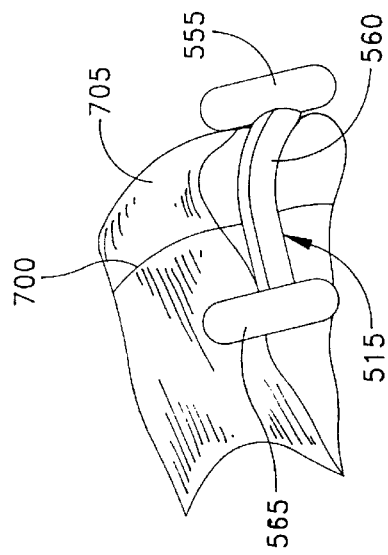
Figure 39:
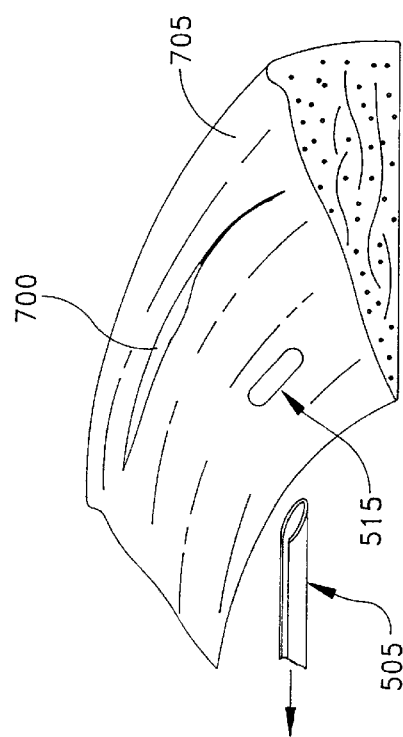

Next, the distal end of applicator 5 is advanced through an arthroscopic cannula which has been inserted in the knee. As this occurs, collar 510 helps keep fastener 515 in place on the applicator. The distal tip of needle 505 is aligned with the pre-measured spot on the meniscus, and then the needle is thrust into meniscus 705 and across tear 700 in the manner shown in FIG. 37. Collar 510 acts as a stop to limit penetration of needle 505 into the tissue, and simultaneously provides compression to meniscus 705 so as to close tear 700. Then, while keeping pressure on the handle of applicator 5, the user depresses trigger 220 (FIGS. 9 and 10) so as to cause push rod 205 to advance. The distal end of push rod 205 engages head 555 of fastener 515 and ejects it out the distal end of needle 505. In this respect it is to be appreciated that the flexible construction of the distal end 205A of push rod 205 permits the push rod to follow the curvature of needle 505 as the fastener is ejected from the needle. As the fastener's leading head 555 exits the far side of meniscus 705, the fastener's trailing head 565 engages the near side of the meniscus (FIG. 38) and draws tear 700 closed. Next, the applicator is withdrawn (FIG. 39) so as to pull the distal tip of needle 505 from meniscus 705, thereby leaving fastener 515 in place so as to hold tear 700 closed (FIG. 40).

Thereafter, needle 505 (sans fastener 515) can be inserted back into its associated tray 600, lock lever 420 raised so as to retract the distal end of sleeve 405 and release needle 505, and then the needle dismounted from chuck 305, whereupon tray 600 and needle 505 can be disposed of in the traditional manner in a so-called "sharps" container.

Modifications Of The Preferred Embodiment

It is, of course, possible to modify the preferred embodiment discussed above without departing from the scope of the present invention.

Thus, for example, it is possible to use the present invention in a procedure other than the one described above, e.g., one might use the present invention to attach two pieces of tissue in the chest or abdomen.

Figure 42:
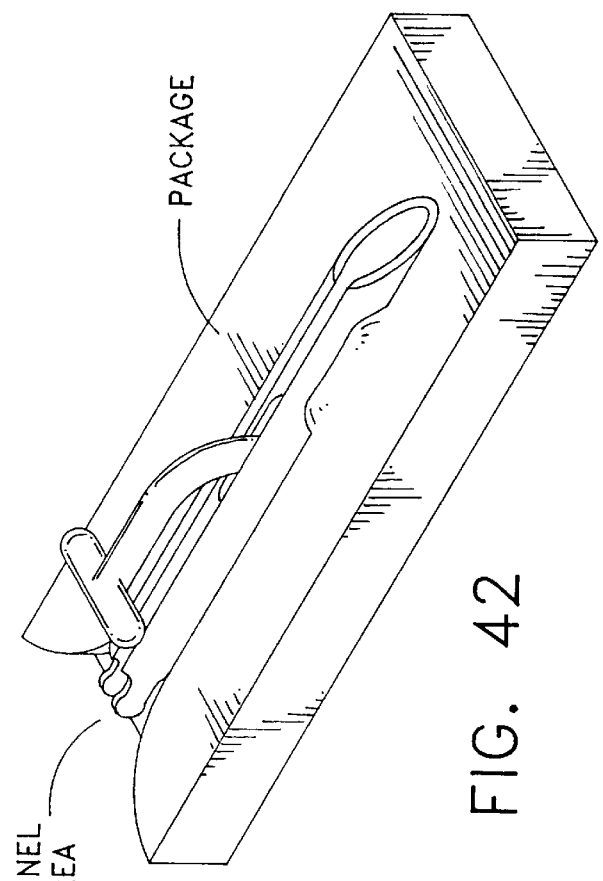
FIG. 42 shows an alternative tray which may be used in connection with the alternative needle assembly shown in FIG. 41.
Figure 41:
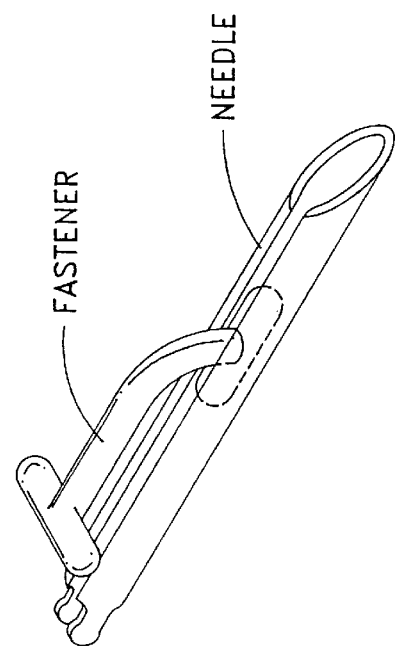
FIG. 41 shows an alternative needle assembly which may be used in connection with the present invention.

Or one might form needle assembly 500 so that it incorporates a straight needle 505A (FIG. 41) rather than the curved needle 505 discussed above. Of course, in such a situation the configuration of tray 600 may also be changed, such as that shown in FIG. 42. Furthermore, in such a situation the distal end 205A of push rod 205 could be formed so as to be relatively rigid, since it would not need to traverse a curved arc as in the case where a curved needle is used.

Figure 43:
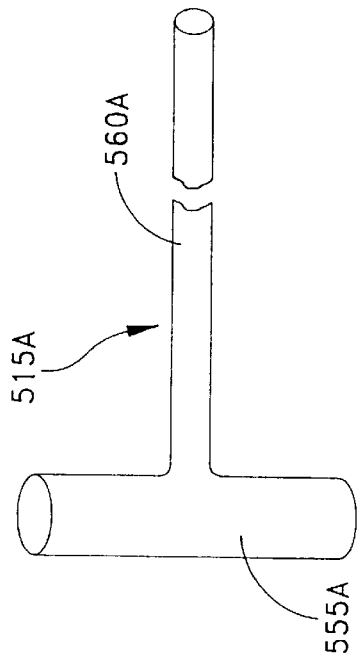
FIG. 43 shows an alternative type of fastener which may be used in conjunction with the present invention.

Or it is possible to use the present invention with a T-type fastener 515A of the sort shown in FIG. 43, rather than with the H-type fastener 515 described above.

Or the distal end 205A of push rod 205 might be formed out of a flexible plastic, rather than as a flexible spring.

Figure 45:
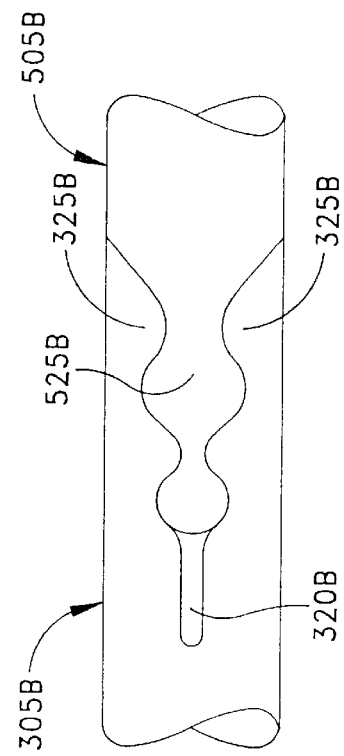
FIGS. 44–46 are schematic views showing several possible alternative constructions for the applicator's needle and chuck assemblies.
Figure 44:
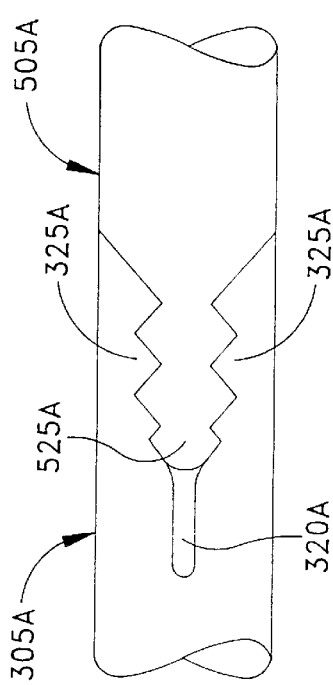
Figure 46:
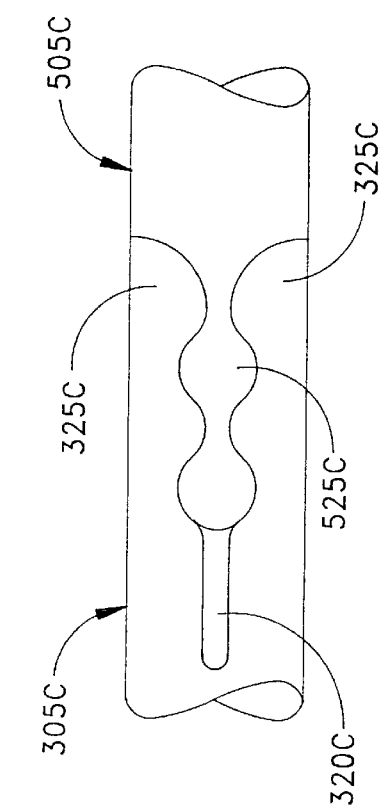

Furthermore, it is possible to vary the configuration of the chuck's slots 320 and the needle's tabs 525, e.g., they may be formed in the manner of slot 320A and tab 525A shown in FIG. 44, or the slot 320B and tab 525B shown in FIG. 45, or the slot 320C and tab 525B shown in FIG. 46. Still other slot and tab configurations will be obvious to a person skilled in the art in view of the teachings of the present invention. In essence, slots 320 and tabs 525 may have many different configurations, so long as (i) the slots 320 a nd tabs 525 are mirror configurations, and (ii) tabs 525 have an enlargement toward their distal end which is received in a corresponding enlargement displaced from the distal end of chuck 305.

Furthermore, while in the foregoing discussion slots 320 have been described and illustrated as being formed in chuck 305, and tabs 525 have been described and illustrated as being formed on needle 505, their dispositions might be reversed, i.e., slots 320 might be formed in needle 505 and tabs 525 might be formed on chuck 305.

Also, collar 510 might be omitted from needle assembly 500 if desired.

Still other changes of this type will be obvious to a person skilled in the art and are considered to be within the scope of the present invention.

What is claimed is:

1. An applicator for deploying a fastener into tissue, the fastener including a head portion and a filament portion extending from the head portion, said applicator comprising:
   an actuator;
   a chuck;
   an elongated hollow needle member;
   a push rod; and
      connector means for interconnecting said needle member and said chuck, said connector means comprising a first part including resilient walls defining an axially open cavity having an enlarged inner portion, and a second part having an inner neck portion and an enlarged outer portion adapted for releasable locking engagement within said enlarged inner portion of said first part;
      said elongated hollow needle member having a pointed distal end portion, a slotted portion for releasably retaining the head of the fastener, and a proximal portion defining one part of said connector means;
      a sleeve member engaging said actuator and movable axially around said distal portion of said chuck and said proximal portion of said elongated hollow needle member so as to encircle said first and second parts of said connector means and thereby lock said first and second parts of said connector means together so as to prevent inadvertent separation thereof;
      said chuck having a proximal portion fixedly attached to said actuator and a distal portion comprising the other part of said connector means;
      said push rod having a distal end portion adapted for reciprocal lengthwise movement in said needle member; and,
      said actuator including means for moving said push rod in said needle member so as to eject the head portion of the fastener from said slotted portion of said needle member.

2. An applicator according to claim 1 wherein said hollow needle member is curved, and said distal end portion of said push rod is sufficiently flexible to move lengthwise within said needle member.

3. An applicator according to claim 1 wherein said sleeve member is withdrawable from said connector means so as to permit separation of said first and second parts of said connector means from one another.

4. An applicator according to claim 4 wherein said actuator is provided with a lever connected to said sleeve, said lever being manipulable relative to said sleeve so as to move said sleeve selectively between a first position encircling said first and second parts of said connector means and a second position not encircling said first and second parts of said connector means.

5. An applicator according to claim 1 wherein said actuator comprises a spring biased trigger connected to said push rod, and said trigger is manipulable against its spring bias to move said push rod.

6. An applicator according to claim 1 wherein said distal end portion of said push rod comprises a flexible spring which is substantially incompressible.

7. An applicator according to claim 1 wherein said first part of said connector means comprises a pair of opposing leg portions formed in said distal portion of said chuck, said leg portions defining a pair of opposing recesses, and said second part of said connector means comprises at least one tab attached to said needle at said neck portion and having at the free end thereof an enlarged portion complementarily shaped relative to said recesses, said leg portions being sufficiently resilient to permit said tab to enter therebetween, and said enlarged portion to enter between said recesses.

8. An applicator according to claim 7 wherein said applicator further comprises a sleeve member disposed around said chuck and movable axially of said chuck so as to encircle said first and second parts of said connector means and thereby prevent the inadvertent separation of said first and second parts of said connector means from one another.

9. An applicator according to claim 8 wherein said push rod is disposed within said chuck and said needle member and movable axially of said chuck and said needle member so as to effect said ejection of said fastener head portion from said needle member.

10. An applicator according to claim 7 wherein said second part of said connector means comprises two tabs extending proximally from diametrically-opposing sides of said hollow needle member respectively, which tabs are adapted to be received by said first part of said connector means defined by said chuck.

11. An applicator according to claim 4 wherein said sleeve is spring-biased toward said second position.

12. An applicator according to claim 2 wherein said distal end portion of said push rod is formed out of a selected one of metal, plastic, and a composite thereof.

13. An applicator according to claim 1 wherein said applicator further comprises a collar mounted on said needle member for releasably holding the fastener's filament portion to said needle member.

14. An applicator according to claim 13 wherein said collar is arranged so as to engage and bear against a tissue surface when said needle member is inserted into the same.

15. A method for deploying a fastener into mammalian tissue, said method comprising the steps of:

providing an applicator for deploying a fastener into tissue, the fastener including a head portion and a filament portion extending from the head portion, said applicator comprising:
an actuator;
a chuck;
an elongated hollow needle member;
a push rod;
a sleeve; and
connector means for interconnecting said needle member and said chuck, said connector means comprising a first part including resilient walls defining an axially open cavity having an enlarged inner portion, and a second part having an inner neck portion and an enlarged outer portion adapted for releasable locking engagement within said enlarged inner portion of said first part;
said elongated hollow needle member having a pointed distal end portion, a slotted portion for releasably retaining the head of the fastener, and a proximal portion defining one part of said connector means;
said chuck having a proximal portion fixedly attached to said actuator and a distal portion comprising the other part of said connector means;
said push rod having a distal end portion adapted for reciprocal lengthwise movement in said needle member; and,
said actuator including means for moving said push rod in said needle member so as to eject the head portion of the fastener from said slotted portion of said needle member; and
said sleeve surrounding said chuck and being movable relative to said actuator between a first position surrounding said second connector means and a second position not surrounding said second connector means;
placing the head portion of the fastener within said slotted portion of said hollow needle member;
interconnecting said first and second parts of said connector means so as to attach said needle member to said chuck;
sliding said sleeve from said second position to said first position such that said sleeve resides over said interconnected first and second parts of said connector means so as to prevent inadvertent separation of said needle member from said chuck;
advancing said needle member to a point whereat the needle member slotted portion extends through an area in which placement of the fastener is desired;
manipulating said actuator so as to move said push rod distally so as to engage said fastener head portion and eject said head portion of the fastener from the slotted portion of said needle member; and
removing said needle member from said tissue.

16. A method according to claim 15 further comprising the additional steps of sliding said sleeve from said first position to said second position, disconnecting said needle member from said chuck, and disposing of said needle member.

* * * * *